US006849249B2

(12) United States Patent
Goldstein et al.

(10) Patent No.: US 6,849,249 B2
(45) Date of Patent: Feb. 1, 2005

(54) OCULAR DIAGNOSIS OF ALZHEIMER'S DISEASE

(75) Inventors: Lee E. Goldstein, Marblehead, MA (US); Leo T. Chylack, Jr., Duxbury, MA (US)

(73) Assignees: The Brigham and Women's Hospital, Inc., Boston, MA (US); The General Hospital Corporation, Boston, MA (US)

( * ) Notice: Subject to any disclaimer, the term of this patent is extended or adjusted under 35 U.S.C. 154(b) by 281 days.

(21) Appl. No.: 10/132,779

(22) Filed: Apr. 25, 2002

(65) Prior Publication Data

US 2002/0182152 A1 Dec. 5, 2002

Related U.S. Application Data

(60) Provisional application No. 60/287,124, filed on Apr. 27, 2001.

(51) Int. Cl.[7] .............................................. A61K 49/00
(52) U.S. Cl. ........................ 424/9.1; 424/9.6; 424/9.61; 600/317
(58) Field of Search ................................ 424/9.6, 9.61, 424/9.1; 600/317, 318, 321, 172; 436/503, 800

(56) References Cited

U.S. PATENT DOCUMENTS

| | | | |
|---|---|---|---|
| 5,171,846 A | * 12/1992 | Gupta ........................ 530/400 |
| 6,001,331 A | * 12/1999 | Caprathe et al. ............. 424/9.1 |
| 6,013,034 A | 1/2000 | Fernandes Da Cunha Vaz et al. ........................... 600/310 |
| 6,054,114 A | 4/2000 | Lansbury, Jr. et al. |
| 6,114,175 A | 9/2000 | Klunk et al. ............. 514/230.5 |
| 6,133,259 A | 10/2000 | Klunk et al. ................... 436/63 |
| 6,168,776 B1 | 1/2001 | Klunk et al. ................ 424/1.11 |
| 6,198,532 B1 | 3/2001 | Cabib et al. ................. 356/346 |
| 6,329,531 B1 | * 12/2001 | Turner et al. ................ 548/455 |
| 6,423,270 B1 | 7/2002 | Wall |
| 6,600,017 B1 | * 7/2003 | Glabe et al. ................. 530/345 |
| 2002/0091321 A1 | * 7/2002 | Goldstein et al. ........... 600/476 |
| 2002/0098153 A1 | * 7/2002 | Allen et al. .............. 424/9.364 |

FOREIGN PATENT DOCUMENTS

WO          98/22146          5/1998

OTHER PUBLICATIONS

Frederikse, PH, *Amyloid–like protein structure in mammalian ocular lenses*, Curr. Eye Res. 20(6):462–468, 2000.
Klunk et al., *Development of small molecule probes fro the beta–amyloid protein of Alzheimer's disease*, Neurobiol. Aging 15(6):691–698, 1994.
Link et al., *Visualization of fibrillar amyloid deposits in living, transgenic Caenorhabditis elegans animals using the sensative amyloid dye, X–34*, Neurobiol Aging 22(2):217–226, 2001.

Pettergrew et al., *Clinical and neurochemical effects of acetyl–L–Canitine in Alzheimer's disease,* Neurobiol. Aging 16(1):1–4, 1995.
Selkoe, DJ, *Toward a comprehensive tehory for Alzheimer's disease. Hypothesis: Alzheimer's Disease is caused by the cerebral accclumulation and cytotoxicity of amyloid β–Protein*, Annal. N.Y. Acad. Sci. 924:17–25, 2000.
Skovronsky et al., *In Vivo detection of amyloid plaques in a mouse model of Alzheimer's diesease*, Proc. Natl. Acad. Sci. USA 97(13): 7609–7614.
Siik et al., *autoflourescense in cataracious human lens and its relationship to ligth scatter*, Acta. Ophthamol. (Cophen) 71(3):388–392; 1993.
Siik et al., *Influence of lens autoflourenscense on retinal nerve fiber layer evaluation*, Acta. Ophthamol. Scand., 75(5):524–527, 1997.
Siik et al., *Lens autoflourescence and light scatter in relation to the lens opacities classification system LOCS III*, Acta Ophthamol. Scand. 77(5):509–514, 1999.
Siik et al, *Lens autoflourescence in ehalthy individuals*, Acta. Ophtamol. (Copenh) 69(2):187–192, 1991.
Siik et al, *Light scatter and cateratous human lense*, Acta. Ophthamol. (Copenh) 70(3):383–388, 1992.
Styren et al., *X–34, a florescent derivative of Congo red: a novel histochemical stain for Alzheimer's disease pathology*, J. Histochem. Cytochem 48(9): 1223–1232, 2002.
Kauffman et al., *Clinoquinol (Iodochlorhydroxyquin, Vioform)and Iodoquinol Diiodohydroxquin): Blindness and Neuropathy (RE9198)*, Pediatrics 86(5):797–798, 1990.
Bacskai, et al. (2002). J. Cereb Blood Flow &Metabol 22: 1035–1041.
Christie, et al. (2001) J Neurosci 21: 858–864.
Kung, et al. (2002). Brain Res 956: 202–210.
Kung, et al. (2002) J Mol Neurosci 19: 7–10.
Klunk, et al. (2001). Life Sci 69: 1471–1484.
Klunk, et al. (2002), J Neuropathol Exp Neurol 61: 797–805.
Klunk, et al. (2003). J Neurosci 23: 2086–2092.
Lee, Chi–Wan (2001). J Med Chem 44: 2270–2275.
Mathis, et al. (2002), Biorganic & Medic Chem Lett 12: 295–298.
McLellan, et al. (2003). J Neurosci 23: 2212–2217.
The International Search Report for PCT/ US 02/12945, mailed Dec. 12, 2002.
Helmuth, Laura (2002). Science 297: 752–753.
Lewis, Ricki (2002). The Scientist 16.
Burggren and Bookheimer (2002). Curr Top Medic Chem 2: 385–393.

* cited by examiner

*Primary Examiner*—Michael G. Hartley
(74) *Attorney, Agent, or Firm*—Mintz, Levin, Cohn, Ferris, Glovsky and Popeo, P.C.; Ingrid A. Beattie

(57) ABSTRACT

The invention features a method of diagnosing or providing a prognosis regarding the state of Alzheimer's Disease in a mammal by contacting an ocular tissue with a detectably-labeled compound, which binds to an amyloid protein. An increase in binding of the compound to the ocular tissue compared to a normal control level of binding indicates that the mammal is suffering from or is at risk of developing Alzheimer's Disease.

17 Claims, No Drawings

OCULAR DIAGNOSIS OF ALZHEIMER'S DISEASE

This application claims priority to U.S. provisional application No. 60/287,124 filed Apr. 27, 2001, the entire contents of which is hereby incorporated by reference.

TECHNICAL FIELD

This invention relates to neurodegenerative disease.

BACKGROUND OF THE INVENTION

Alzheimer's Disease (AD) is a chronically progressive degenerative disorder of aging and is a major contributor to morbidity and modality in the elderly. AD currently accounts for about 70% of all cases of dementia and affects some 2–4 million Americans. As many as 9 million Americans may have AD by the year 2050. Epidemiological studies have estimated that if AD could be delayed by 5 years, the incidence and prevalence of AD would be cut in half. Development and execution of future therapies for AD will rely on sensitive and early diagnosis of the disease. Although much is known about the disease, there are no currently available means of early diagnosis or effective treatment.

SUMMARY

The invention provides a non-invasive method for early and reliable detection of AD or a pre-morbid neurodegenerative state. The diagnostic method is carried out by contacting an ocular tissue of a mammal, e.g., a human subject, with a detectably-labelled compound which binds to an amyloid protein e.g., amyloid-β (Aβ). By "amyloid protein" is meant a protein or peptide that is associated with a AD neuritic senile plaque. Preferably, the amyloid protein is amyloid precursor protein (APP) or a naturally-occurring proteolytic cleavage product. APP cleavage products include Aβ1-40, Aβ2-40, Aβ1-42, as well as oxidized or crosslinked Aβ. The compounds bind to naturally-occurring variants of APP and Aβ, including single nucleotide polymorphic (SNP) variants. An increase in binding of the compound to an ocular tissue, e.g., an intracellular compartment of a lens cell, compared to a normal control level of binding indicates that the mammal is suffering from or is at risk of developing AD. Preferably, the compound binds to Aβ1-42 or another fragment of an amyloid precursor protein (APP). The compounds preferentially bind to amyloid proteins compared to other β-pleated sheet containing proteins. Preferably, the detectably-labelled compound contains a fluorescent probe. For example, the fluorescent probe or fluorophor is a Chrysamine or Chrysamine derivative compound such as {(trans, trans), -1-bromo-2,5-bis-(3-hydroxycarbonyl-4-hyrdoxy)styrlbenzene (BSB)}.

The methods are useful for in vivo drug screening to identify compounds, which inhibit Aβ accumulation in the eye and brain, for pre-morbid staging AD severity, diagnosis, prognosis, and monitoring patient responses to drug therapy for AD. The degree of Aβ aggregation in the cortical region of the eye is directly proportional to neuropathological Aβ deposits in the brain.

An eye tissue of a test subject is contacted with the compound, allowed to penetrate cells in the lens region of the eye, and fluorescence is measured. The cortical region of the eye is evaluated by fluorescent scanning. Alternatively, the aqueous humor, i.e., the clear liquid between the cornea and the lens, of the eye is scanned. An increase of at least 10% over lens fluorescence of a normal control subject (after probe administration) indicates AD or a predisposition thereto. A normal control value typically corresponds to little or no binding of the probe to lens tissue. The level of normal lens fluorescence is the level of fluorescence detected after contacting an eye of a normal, AD-free subject (or population of subjects) with an Aβ-binding detectably-labeled compound. The value is optionally derived by determining the average or mean of values derived from a pool of individuals of subjects known to be free of AD (as well as free of family history or known genetic predisposition thereto). If the probe used emits light in the range of normal human lens autofluroescence (blue-green range), the level of autofluorescence is factored into the reading. For example, a 10% increase in fluorescence (after probe administration) compared to the level in the absence of the probe (autofluorescence) indicates a pathological state or predisposition to developing a neuropathological state. Preferably, baseline autofluorescence is established (prior to probe administration) for each individual.

A diagnostic level of fluorescence is preferably at least 25%, more preferably at least 50%, more preferably at least 100% greater than a normal control value. For example, detection of Aβ-specific probe fluorescence, which is 2-fold or more greater than a normal control value, indicates a pathological state. Since normal human lens tissue autofluoresces in the blue-green range (495 nm/520 nm), the probe preferably emits a wavelength of light outside the blue-green spectra. For example, the fluorescent probe emits a wavelength of light greater than 520 nm, e.g., fluorescence in the red, orange-red, or infrared range. Alternatively, the probe emits a wavelength less than 450 nm, e.g., in the violet or ultra-violet (UV) range.

A method for prognosis of Alzheimer's Disease includes the steps of (a) contacting ocular tissue of a mammal with a compound which binds to an amyloid polypeptide; (b) quantitating binding of the compound to ocular tissue; and (c) comparing the level of binding with a normal control level of binding. Increased levels of binding over time indicates an adverse prognosis. Test patient lens fluorescence after probe administration is compared to endogenous autofluorescence of a non-AD subject (or population of individuals) or the level of fluorescence of a non-AD subject (or population of non-AD subjects) after probe administration. The methods are also used to stage severity of disease, monitor responses to drug treatment, and screen drugs for the ability to inhibit β accumulation. An increased level of fluorescence (indicative of cortical lens Aβ accumulation) indicates a more advanced stage of AD. A reduction in level of fluorescence (indicative of cortical lens Aβ accumulation) over time indicates that a given drug inhibits Aβ accumulation and indicates a positive clinical response to drug treatment.

Also within the invention are detectably-labelled Aβ binding compounds which emit light outside the blue-green range. For example, the binding compounds are fluorescent probes which emit light at a wavelength between 550–700 nm. The compounds contain Texas Red or a derivative thereof.

The compounds, e.g., polypeptide ligands, organic compounds, or inorganic compounds, are isolated or purified. An "isolated" or "purified" composition is substantially free of cellular material or other contaminating proteins from the cell or tissue source from which it is derived, or substantially free from chemical precursors or other chemicals when chemically synthesized. Preferably, a preparation of a compound, e.g., a fluorescent Aβ-binding compound, is at least 75%, more preferably 80%, more preferably 85%, more preferably 90%, more preferably 95%, more preferably 98%, and most preferably 99 or 100% of the dry weight of the preparation.

"Fluorescence" is the phenomenon in which light energy ("exciting light") is absorbed by a molecule resulting in the molecule becoming "excited.". After a predescribed interval such as 1 minute–24 hours, the absorbed light energy is emitted by the excited molecule. The wavelength of the emitted light is typically at a longer wavelength than the exciting light. This emitted light is referred to as fluorescent light. A molecule that exhibits fluorescence is referred to as a "fluorophor." The relationship between wavelengths of light and degree of excitation of a given fluorophor at that wavelength is described by the "excitation spectrum" of the fluorophor. The excitation spectrum is also called the excitation wavelength range. The relationship between the wavelength of light and the intensity of the fluorescence emission at that wavelength is described by the emission spectrum or fluorescence spectrum of the fluorophor. The emission spectrum is also called the emitted wavelength range. The excitation maximum is the wavelength of exciting light at which fluorescence of the fluorophor reaches maximum intensity. The emission maximum is the wavelength of light emitted by the excited fluorophor when its fluorescence is at maximum intensity.

Most fluorophors excited by and emitting visible light have an emission spectrum overlapping their excitation spectrum, although the maximum for each is different. The distance in nanometers between the excitation spectrum maximum and the emission spectrum maximum is known as the "Stokes' shift." Fluorophors with large Stokes' shifts in the visible range work best in this invention. For example, a fluorophor with an excitation maximum of 400 nm and an emission maximum of 700 nm with little or no overlap between the spectra is preferable.

The methods described herein offer several advantages over existing approaches to AD diagnosis. First, the method is carried out ante-mortem and accurately and reliably identifies Aβ accumulation in living tissues. Prior to the invention, reliable detection of deposits were made from studying autopsy samples of the brains of AD patients. Second, the method is non-invasive; no biopsy of tissue is required. The method utilizes physiologically-compatible probes. Moreover, the scanning procedure itself takes a matter of seconds, e.g., 30 seconds–minutes. Finally, the specificity and sensitivity of detection is high because of the unique anatomical pattern of Aβ accumulation, i.e., the cortical region of the lens in a non-diseased state is characterized by little or no protein accumulation/aggregation. Even small amounts of Aβ protein accumulation is stable and easily detectable in this region of the eye.

Other features, objects, and advantages of the invention will be apparent from the description and drawings.

DETAILED DESCRIPTION

The non-invasive ocular diagnostic methods described herein facilitate diagnosing, prognosing, and monitoring AD and related neurodegenerative disorders, which are mediated by accumulation of amyloid proteins. The disease process involves pathogenic accumulation of Aβ peptides in vulnerable regions of the brain. The invention is based on the discovery that these same Aβ peptides accumulate as microaggregates in ocular cells and, in particular, within the cortical region of the lens in AD patients. In addition to accumulation in the cortex of the eye, Aβ accumulates in the aqueous humor of the eye, e.g., in the anterior chamber. Progression of the disease leads to cell death and accumulation of extracellular Aβ peptides. Protein aggregation may progress to the development of a relatively rare cataract ("supranuclear", or deep cortical, cataract). Such supranuclear cataracts were detected in a transgenic mouse model of AD and in post-mortem lenses from human patients neuropathologically confirmed for AD. The diagnostic methods of the invention are tools by which to monitor Aβ aggregation and accumulation in the lens as a biomarker for similar events occurring in considerably less accessible cerebral compartments.

Chrysamine G and derivatives thereof are known in the art (e.g., U.S. Pat. Nos. 6,133,259; 6,168,776; 6,114,175). These compounds bind to Aβ peptides, but are not fluorescent. The diagnostic methods utilize a highly lipophilic fluorescent amyloid-binding Chrysamine G derivative to detect Aβ peptides in the eye. After contacting ocular tissue with an Aβ-specific probe, non-invasive scanning using standard ocular fluorphotometric techniques reveals the degree of binding. Ocular fluorimeters and other eye imaging devices are known in the art (e.g., U.S. Pat. Nos. 6, 198,532 and 6,013,034).

The methods take advantage of bioavailable lipophilic fluorescent probes. Such fluorophors and probes are commercially-available, e.g., from Molecular Probes, Inc. Eugene, Oreg. Some dyes, e.g., X-34 or {(trans, trans), -1-bromo-2,5-bis-(3-hydroxycarbonyl-4-hyrdoxy) styrlbenzene (BSB)} (Styren et al., 2000, J. Histochem. 48:1223–1232; Link et al., 2001, Neurobiol. Aging 22:217–226; and Skrovonsky et al., 2000, Proc. Natl., Acad. Sci. U.S.A. 97:7609–7614) have been used to analyze brain tissue (but not eye tissue). These probes emit light in the blue-green range, thus the level of fluorescence, which is diagnostically relevant, exceeds the amount of human lens autofluorescence in the blue-green range.

The probes utilized in the diagnostic methods specifically bind to Aβ and (Aβ-associated proteins relative to other β-pleated sheet-containing proteins or polypeptides The probes are applied to the eye in a liquid or ointment form. The lipophilicity of the compounds facilitates penetration the intervening structures. The compounds bind with high avidity to accumulations of Aβ within the lens and other ocular structures. For example, the compounds are formulated in a solution with an excipient, e.g., DMSO, to improve tissue and cellular penetration of the fluorescent Aβ-binding compound. After contacting the eye with the compound, the compond is allowed to penetrate ocular tissues for a period of time, e.g., 1 minute to 5 hour, prior to fluorescent scanning of the eye. Preferably, the eye is contacted with the compound for at least one hour prior to fluorometric scanning. The eye may be contacted with the probe for up to a day or more prior to scanning. Ratiometric and other analyses of fluorophotometric signals before and after ocular application and distribution of the fluorescent probes within specific subregions of the ocular structures quantitatively reveal the degree and localization of Aβ accumulations associated with the AD disease state. An increase in the amount of accumulated Aβ peptides compared to a normal control value indicates a neurodegenerative condition such as AD.

The region of the lens in which an AD-associated supranuclear cataract forms is not predisposed to form high molecular weight aggregates compared to the nuclear region of the lens. In addition, lens proteins, once formed, are uniquely stable for long periods of time. Thus, proteins and peptides in the lens are not readily cleared and tend to accumulate, whereas in the brain multiple mechanisms are involved in the clearance of deleterious Aβ peptides. Thus, the unique situation of lens Aβ promotes early accumulation relative to the brain. This property of the lens increases the accuracy and reliability of detecting Aβ-mediated aggregation and accumulation very early in the course of the disease (e.g., prior to the appearance of overt cognitive or neurological symptoms).

Amyloid Proteins

AD is characterized by severe oxidative damage and pathologic accumulation of insoluble protein in vulnerable brain regions. The toxic amyloid Aβ peptides are generally considered to be major pathogenic participants in AD. These various peptides are generated by cleavage of a larger protein called the β-amyloid precursor protein (APP) (Selkoe et al., 2000, Annal. of N.Y. Acad. Sci. 924:17–25). Proteins called presenilins (PS1, PS2) may mediate cleavage. Other neuritic plaque-associated proteins include β-amyloid secretase enzymes I and II (BASE I and II) which associate with amyloid proteins. Some of the resulting Aβ peptides are more toxic than others. Elevation of specific Aβ peptides in the brain is believed to be causally associated with all known forms of AD. This generally accepted "Aβ hypothesis" states that Aβ generation, deposition and/or accumulation in the brain is an important final common pathway which underlies the disease process in this devastating neurological disorder.

Amyloid proteins (Aβ, APP, PS1, PS2) are also expressed in the mammalian lens. Aβ aggregation occurs both inside and outside cells, depending upon the state of progression of the neurodegenerative disease. Aβ is capable of aberrantly interacting with proteins in the lens, such as the long-lived α-crystallins. The diagnostic methods described herein are based on the following observations: i) Aβ peptides accumulate in specific subregions of the lens, ii) Aβ peptides potently promote lens protein aggregation, and iii) a distinctive deep supranuclear zonular cataract is associated with Aβ overexpression in a well-characterized animal model of AD, the amyloid-bearing APP-mutant Tg2576 transgenic mouse, and in post-mortem lenses derived from human patients having been diagnosed independently and neuropathologically with AD.

Fluorescent Detection of AD-Associated Protein Accumulation in the Eye

The data described herein indicate that in vivo examination of lens proteins yield diagnostically-relevant information about Aβ accumulution, which cannot be obtained from less accessible organs such as the brain. A significant advantage of these methods is that they are non-invasive. The non-invasive methods are useful in in vivo drug screening, diagnosing, prognosing, and monitoring responses of AD patients to therapeutic intervention. The technique takes advantage of a lipophilic fluorescent high affinity Aβ-binding probe such as {(trans, trans), -1-bromo-2,5-bis-(3-hydroxycarbonyl-4-hydroxy)styrlbenzene (BSB)}. This compound (as well as lipophilic fluorescent Aβ-binding derivatives) is applied to the eye and allowed to distribute into the lens.

Unlike other methods, which use relatively non-specific amyloidophilic probes, e.g., Congo Red or thioflavine, the present methods employ probes, which are highly specific for Aβ peptides. The other amyloidophilic probes bind to β-pleated sheet protein structures present in the eye, whereas the Chrysamine-based probes specifically bind to Aβ and other fragments of APP. Chrysamine G and other amyloid-binding derivative of Congo Red are useful as the amyloid binding moiety of the probe; a detectable label, e.g., a fluorophor is attached to allow fluorescent scanning.

Chrysamine and other Congo Red derivatives bind to amyloid proteins through a bedentate attachment spanning several amyloid peptide chains.

The amount of Aβ-binding along the optical axis is monitored by scanning fluorophotometric techniques. Fluorescence along the optical axis is measured prior to application of the probe to determine baseline autofluorescence. Fluorescence is then measured again after application of the probe. Fluorescence is measured in the supranuclear deep cortical region of the anterior and posterior lens as well as in the nuclear region. The ratio of cortical fluorescence to nuclear fluorescence before application of the probe is compared to the ratio after probe application. For example, the ratio of cortical to nuclear fluorescence before probe application is 2:2; after probe application, the ratio is 10:2. The comparison indicates Aβ accumulation (and a diagnosis of AD or a predisposition to developing AD). A normal control value minimal or no detetable fluorescence in the cortical region after probe administration. Binding of a lipophilic fluorescent Aβ-binding probe, as indicated by an increased fluorescent signal in the cortical lens region compared to the nuclear region, yields a metric which is correlated with disease presence or absence. The degree of Aβ accumulation is greater and more rapid within the lens compared to other tissues. This accumulation is indicative of the stage of the disease, i.e., greater accumulation is directly correlated with a more advanced stage of AD or a related neurodegenerative state. The magnitude of fluorescence above baseline autofluorescence correlates with disease severity. These binding data serve as a biological indicator or biomarker of Aβ deposition within the brain.

Aβ-specific probes are lipophilic and relatively uncharged. In contrast, antibody probes or antibody fragments are not suitable in the assay, because of their large molecular mass and charge The lipophilic nature of the probes mediates efficient access to eye tissues and across the lipophilic barrier of the eye and cell membranes of eye structures. In addition, lipophilicity facilitates access to the intracellular compartments of cells in the lens region of the eye. This aspect of the probes is critical for early disease detection, because in the early stages of AD, Aβ accumulates inside the cells rather than extracellularly. Only as the disease progresses and cells die, do extracellular accumulations or plaques become evident.

In addition to the probes described above which emit light in the blue-green region of the light spectrum, the methods also utilize other probes, which emit a fluorescent signal outside (longer or shorter) the range of normal lens autofluorescence (495 nm/520 nm). Various small molecular fluorophors are conjugated to amyloid binding compounds, e.g., Chrysamine G or clioquinol, using methods known in the art. For example, long wave fluorophors, e.g., Texas Red and derivatives thereof, are used. Such dyes allow scanning at wavelengths, e.g., in the far infrared range, without interference of normal lens autofluorescence.

EXAMPLE 1

AD-Associated Cataract Formation

Advanced Aβ accumulation in eye tissues leads to cataract formation. Unlike the brain, the region of the lens of the eye to be scanned is characterized by low protein turnover. Proteins in the lens are stable and not cleared for decades. Thus, increased production of APP proteins, e.g., Aβ peptides, are detected very early in the progression of the disease and remain stable and detectable for long periods of time.

AD is characterized by cerebral accumulation of protein aggregates composed of Aβ peptides. Prior to or concurrently with accumulation of Aβ peptides in the brain, the peptides are accumulate and are detectable n eye tissues. AD-associated deep cortical (supranuclear) cataract formation have now been detected in lenses from postmortem human AD patients and amyloid-bearing Tg2576 transgenic mice.

Aβ peptides in the lens were analyzed using slitlamp photomicroscoscopy, Aβ-Immunogold electron microscopy (EM), quantitative Western blot, co-immunoprecipitation, and in vitro turbidometry. Lenses from neuropathologically-confirmed AD cases show cataracts within the supranuclear lens region. In normal control subjects, cataract formation in this region is rare. Aβ accumulation and supranuclear cataracts were detected in post-mortem lens tissue of AD patients and in Tg2576 transgenic mice, an art-recognized model for human AD. EM studies of human AD lenses showed clusters of Aβ-immunoreactive microaggregates within the cortical fiber cell cytoplasm. Most lens Aβ is associated with other proteins, including Aβ-crystallin. Aβ potently promotes human lens protein aggregation through trace metal-dependent oxidative mechanisms.

These data indicate that intracellular Aβ protein aggregation leads to supranuclear cataract formation. Accumulation of Aβ-associated lens aggregates occurs early in AD and remain in situ. Thus, the lens provides a peripherally accessible "molecular window" on cerebral amyloidogenic processes. The non-invasive diagnostic and monitoring approaches for quantitating Aβ in the eye allow early and reliable identification of AD, patients with sub-clinical AD or who are predisposed to developing a neurdegenerative condition such as AD.

EXAMPLE 2

Amyloidogenic, Cytotoxic, and Redox Profiles of the Aβ Peptides

Age-related cataracts (ARC) and Alzheimer's disease (AD) are characterized by oxidative damage and pathologic accumulation of aggregated protein. Aβ peplides and AD-associated proteins are expressed in lens. Metalloprotein reactions correlate with amyloidogenic, cytotoxic, and redox profiles of the different Aβ peptides.

The contribution of Aβ peptides and metalloprotein chemistry to lens protein aggregation was studied as follows. Lenses from amyloid-bearing Tg+ transgenlc (vs Tg−) mice and human specimens were examined by slit lamp photomicroscopy and analyzed for Aβ and APP by quantitative Western blot, EM, and immunohistochenistry. In vitro aggregation studies were carried out by incubating soluble total lens protein (TLP) with synthetic Aβ peptides, chelators, antioxidant scavengers, followed by optical density analysis, Western blot; and standard amyloid assays.

The data indicated that 1) Aβ and APP are expressed in lens; 2) Aβ is found as monomeric, oligomeric, crosslinked, and aggregated species; 3) Tg2576 APP-mutant transgenic mice develop bilateral supranuclear "zonular' cataracts; 4) in vitro TLP aggregation depends on trace metal and reactive oxygen specks (ROS); and 5) Aβ, especially the highly amyloidogenic human Aβ1-42, markedly potentiates TLP aggregation in a metal/ROS-dependent and peptide specific manner. Aβ1-42 in lenses contributes to cataractogenesis and is indicative of AD or a predisposition thereto. The data also suggest that processes which contribute to the development of AD and ARC are biochemically linked.

Metals such as copper, zinc, and iron become strongly associated with Aβ. The metals colocalize with Aβ accumulations or plaques. Accordingly, a lipophilic fluorescent metal chelating agent, e.g., clioquinol, is useful to detect Aβ deposits in the cortical region of the lens. Metal binding compounds are used alone (provided they exhibit detectable fluorescence) or are modified by attachment of a fluorophor to confer or augment fluorescence. The amyloid-binding and metal probes described herein may be administered therapeutically to prevent protein aggregation.

Other embodiments are within the following claims.

What is claimed is:

1. A method of diagnosing Alzheimer's Disease or a predisposition thereto in a mammal, comprising
   (a) contacting an ocular tissue with a detectably-labeled compound, which preferentially binds to an amyloid protein located in said ocular tissue;
   (b) allowing said compound to distribute into the lens; and
   (c) imaging said ocular tissue, wherein said detectably-labeled compound comprises a fluorophor, wherein said detectably-labeled compound is lipophilic, and wherein an increase in binding of said compound to said ocular tissue compared to a normal control level of binding indicates that said mammal is suffering from or is at risk of developing Alzheimer's Disease.

2. The method of claim 1, wherein said fluorophor emits a wavelength of light outside the blue-green spectra.

3. The method of claim 1, wherein said fluorophor emits a wavelength of light greater than 520 rim.

4. The method of claim 1, wherein said fluorophor emits a wavelength of light in the infrared range.

5. The method of claim 1, wherein said fluorophor emits a wavelength less than 450 rim.

6. The method of claim 1, wherein said fluorophor comprises a Chrysamine compound.

7. The method of claim 1, wherein said compound preferentially binds to an amyloid-β (Aβ) polypeptide.

8. The method of claim 1, wherein said compound preferentially binds to Aβ (1–42).

9. The method of claim 1, wherein said fluorophor is {(trans, trans), -1 -bromo-2,5-bis-(3-hydroxycarbonyl-4-hyrdoxy)styrlbenzene (BSB)}.

10. The method of claim 1, wherein said ocular tissue comprises a cortical region of an eye.

11. The method of claim 1, wherein said ocular tissue comprises a supranuclear region of an eye.

12. The method of claim 1, wherein said ocular tissue comprises an aqueous humor region of an eye.

13. The method of claim 1, wherein said increase is at least 10% greater than said normal control value.

14. The method of claim 1, wherein said increase is at least 25% greater than said normal control value.

15. The method of claim 1, wherein said increase is at least 50% greater than said normal control value.

16. The method of claim 1, wherein said increase is at least 100% greater than said normal control value.

17. A method for prognosis of Alzheimer's Disease, comprising
   (a) contacting ocular tissue of a mammal with a compound which preferentially binds to an amyloid polypeptide, wherein said compound comprises a fluorophor and wherein said detectably-labeled compound is lipophilic;
   (b) allowing said compound to distribute into the lens
   (c) imaging said ocular tissue;
   (d) quantitating the level of association of said compound with said ocular tissue; and
   (e) comparing said level of association with a normal control level of association, wherein increasing levels of association over time indicates an adverse prognosis.

* * * * *

UNITED STATES PATENT AND TRADEMARK OFFICE
CERTIFICATE OF CORRECTION

PATENT NO. : 6,849,249 B2
DATED : February 1, 2005
INVENTOR(S) : Goldstein and Chylack It is certified that error appears in the above-identified patent and that said Letters Patent is hereby corrected as shown below:

<u>Column 8,</u>
Lines 24-25, should read:
-- 3. The method of claim 1, wherein said flurophor emits a wavelength of light greater than 520 nm. --
Lines 28-29, should read:
-- 5. The method of claim 1, wherein said flurophor emits a wavelength less than 450 nm. --
Lines 36-38, should read:
-- 9. The method of claim 1, wherein said flurophor is {(trans, trans), -1 -bromo-2,5-bis-(3-hydroxycarbonyl-4-hydroxy)styrlbenzene (BSB)}. --

Signed and Sealed this

Third Day of May, 2005

JON W. DUDAS
*Director of the United States Patent and Trademark Office*